United States Patent
Okubo et al.

(10) Patent No.: US 12,023,658 B2
(45) Date of Patent: Jul. 2, 2024

(54) ZEOLITE, AND CATALYST FOR USE IN PRODUCTION OF AROMATIC HYDROCARBON WHICH COMPRISES SAME

(71) Applicant: TOSOH CORPORATION, Shunan (JP)

(72) Inventors: Amane Okubo, Mie (JP); Tomohiro Hayashi, Mie (JP); Ryo Ishimoto, Mie (JP); Makoto Hanaya, Mie (JP)

(73) Assignee: TOSOH CORPORATION, Shunan (JP)

( * ) Notice: Subject to any disclaimer, the term of this patent is extended or adjusted under 35 U.S.C. 154(b) by 358 days.

(21) Appl. No.: 17/621,773

(22) PCT Filed: Jul. 2, 2020

(86) PCT No.: PCT/JP2020/026089
§ 371 (c)(1),
(2) Date: Dec. 22, 2021

(87) PCT Pub. No.: WO2021/006188
PCT Pub. Date: Jan. 14, 2021

(65) Prior Publication Data
US 2022/0355280 A1 Nov. 10, 2022

(30) Foreign Application Priority Data
Jul. 10, 2019 (JP) .................. 2019-128047

(51) Int. Cl.
*B01J 29/70* (2006.01)
*B01J 21/08* (2006.01)
(Continued)

(52) U.S. Cl.
CPC .............. *B01J 29/70* (2013.01); *B01J 21/08* (2013.01); *B01J 35/23* (2024.01); *B01J 35/40* (2024.01);
(Continued)

(58) Field of Classification Search
None
See application file for complete search history.

(56) References Cited

U.S. PATENT DOCUMENTS 4,520,221 A 5/1985 Hsia Chen
4,568,768 A 2/1986 Nakamura et al.
(Continued)

FOREIGN PATENT DOCUMENTS

JP 62-178530 A 8/1987
JP 01-103917 A 4/1989
(Continued)

OTHER PUBLICATIONS

Al-Eid et al. ("Effect of ZSM-5 Particle Size and Framework Silica-to-Alumina Ratio on Hexane Aromatization", Catalysis Research 2022; 2(4), doi: 10.21926/cr.2204035). (Year: 2022).*
(Continued)

*Primary Examiner* — Ali Z Fadhel
(74) *Attorney, Agent, or Firm* — Sughrue Mion, PLLC

(57) ABSTRACT

Provided are: novel zeolite having an extremely small amount of specific Bronsted acid sites on the surface thereof, which is expected to be useful as a catalyst for the aromatization of a non-aromatic hydrocarbon typified by an aliphatic hydrocarbon; and a catalyst for use in the production of an aromatic hydrocarbon, which comprises the zeolite. Zeolite characterized by satisfying the following requirements (i) to (iii). (i) The zeolite has an average particle diameter of 100 nm or less. (ii) The zeolite is 10-membered ring microporous zeolite. (iii) The amount of the Bronsted
(Continued)

acid sites on the outer surface of the zeolite is 0.1 to 10.0 µmol/g.

9 Claims, 1 Drawing Sheet

(51) Int. Cl.
  *B01J 35/23* (2024.01)
  *B01J 35/40* (2024.01)
  *C07C 2/42* (2006.01)
(52) U.S. Cl.
  CPC .......... *C07C 2/42* (2013.01); *C07C 2521/08* (2013.01); *C07C 2529/70* (2013.01)

(56) References Cited

U.S. PATENT DOCUMENTS

| | | | |
|---|---|---|---|
| 4,914,247 | A | 4/1990 | Sekizawa et al. |
| 5,294,579 | A | 3/1994 | Ohashi et al. |
| 5,354,933 | A | 10/1994 | Ohashi et al. |
| 5,968,342 | A | 10/1999 | Tsunoda et al. |
| 9,687,827 | B2 | 6/2017 | Otaka et al. |
| 2016/0199824 | A1* | 7/2016 | Yoshida .................. C07C 5/13 585/484 |

FOREIGN PATENT DOCUMENTS

| | | |
|---|---|---|
| JP | 3264447 B2 | 3/2002 |
| JP | 3741455 B2 | 2/2006 |
| JP | 6029654 B2 | 11/2016 |
| JP | 2018-145085 A | 9/2018 |
| JP | 2019-026571 A | 2/2019 |

OTHER PUBLICATIONS

Liu et al. ("Interplay Between Particle Size and Hierarchy of Zeolite ZSM-5 During the CO2-to-aromatics Process", ChemSusChem 2023, 16, e202300608 (p. 1-7)). (Year: 2023).*
International Search Report of PCT/JP2020/026089, dated Sep. 24, 2020 [PCT/ISA/210].
Communication, dated Jan. 20, 2022, issued by the International Bureau in International Application No. PCT/JP2020/026089.
Yongbeom Seo et al., "Characterization of the Surface Acidity of MFI Zeolite Nanosheets by $^{31}$P NMR of Adsorbed Phosphine Oxides and Catalytic Cracking of Decalin," ACS Catalysis, vol. 3, No. 4, Mar. 13, 2013, pp. 713-720 (8 pages total), XP093091096.
Lingqian Meng et al., "A dual-templating synthesis strategy to hierarchical ZSM-5 zeolites as efficient catalysts for the methanol-to-hydrocarbons reaction", Journal of Catalysis, vol. 361, May 1, 2018, pp. 135-142 (8 pages total), XP093091505.
H. T. Yan et al., "Hybrid catalysts used in the Catalytic Steam Cracking process (CSC): Influence of the pore characteristics and the surface acidity properties of the ZSM-5 zeolite-based component on the overall catalytic performance", Applied Catalysis A: General, vol. 375, No. 1, Feb. 26, 2010, pp. 63-69 (7 pages total), XP026878430.
Liying SUN et al., "Direct synthesis of hierarchical ZnZSM-5 with addition of CTAB in a seeding method and improved catalytic performance in methanol to aromatics reaction," Catalysis Today, vol. 316, Oct. 1, 2018, pp. 91-98 (8 p. total), XP093091321.
Extended European Search Report issued Jan. 31, 2024 in Application No. 20836396.0.

* cited by examiner

ZEOLITE, AND CATALYST FOR USE IN PRODUCTION OF AROMATIC HYDROCARBON WHICH COMPRISES SAME

CROSS REFERENCE TO RELATED APPLICATIONS

This application is a National Stage of International Application No. PCT/JP2020/026089, filed Jul. 2, 2020, claiming priority based on Japanese Patent Application No. 2019-128047, filed Jul. 10, 2019.

TECHNICAL FIELD

The present invention relates to a novel zeolite which is a 10-membered ring pore zeolite having a specific amount of Bronsted acid sites on the outer surface and a catalyst for producing aromatic hydrocarbons comprising the same. More specifically, the present invention relates to a novel zeolite which is a 10-membered ring pore zeolite, which acts as a catalyst for producing aromatic hydrocarbons with excellent production efficiency of aromatic hydrocarbons due to its specific average particle diameter and a small amount of Bronsted acid sites on the outer surface.

BACKGROUND ART

In many cases, benzene, toluene, and xylene (hereafter occasionally generically named and expressed as aromatic compounds) are obtained by cracking raw oil (for example, naphtha and the like) obtained from petroleum refining with a thermal cracker, and separating and refining aromatic compounds from the resulting pyrolysis products by distillation or extraction. In the production of aromatic compounds by these processes, aliphatic and/or alicyclic hydrocarbons are contained as pyrolysis products other than aromatic compounds. That is, aliphatic and/or alicyclic hydrocarbons are produced simultaneously with the production of aromatic compounds. Therefore, the amount of aromatic compounds produced is adjusted according to the amount of aliphatic and/or alicyclic hydrocarbons produced, and inevitably is limited by their production amount.

Zeolites are widely used industrially as the uses such as petrochemical catalysts, exhaust emission reduction catalysts for internal-combustion engines or the like, adsorbents, and the like. In the case of industrial use, zeolites have been used as zeolite molded articles in which zeolites and binders are complexed for improvement in durability and handleability. The zeolite molded articles are produced by mixing binders (for example, silica, clay minerals, and the like) and zeolites, forming the mixture into predetermined shapes, and then sintering it by high temperature calcination.

Medium pore zeolites and zeolite complexes have been used as highly selective catalysts using pores in a size equivalent to aromatic compounds. As examples using representative MFI type zeolites of such zeolites as catalysts, the disproportionation of toluene, the isomerization of xylene, and the like have been proposed. These reactions mainly use the characteristics of micropores of zeolites. The micropores of medium pore zeolites have an inlet size of around 0.5 nm, and it is considered that the micropores function as effective reaction sites of molecules having a molecular size approximate to this pore size.

Methods for producing aromatic compounds by contacting aliphatic or alicyclic hydrocarbon raw materials with a catalyst mainly comprising a medium pore zeolite at a temperature of around 400° C. to around 800° C. have been proposed (for example, Patent Literatures 1 and 2). These production methods have the effect of enabling producing aromatic compounds from non-aromatic compounds which are surplus hydrocarbons with low added value compared to the raw material used in the method for producing aromatic compounds by thermal cracking. Meanwhile, these methods still have a problem with respect to production efficiency and selectivity.

Further, in reaction using a zeolite as a catalyst, reactions on acid sites on the surface (outer surface) of zeolite are also known, and these reactions are generally considered as unselective reactions. These unselective reactions often induce a decrease in product yield, a decrease in product selectivity, the deactivation of catalysts due to coke deposition, and the like, and it is determined that these unselective reactions are undesirable.

As a method of inhibiting such unselective reactions, a zeolite in which acid sites on the surface are removed has been proposed (for example, refer to Patent Literature 3). Furthermore, a method of extracting aluminum on the surface or covering the surface with a bulky reagent have been proposed. Specifically, a method for covering a zeolite having an MFI structure with a silicate to produce p-xylene selectively (for example, refer to Patent Literature 4), methods for covering acid sites on the surface of zeolites with bulky dialkylamine reagents (for example, refer to Patent Literatures 5 and 6), and the like have been proposed.

CITATION LIST

Patent Literature

Patent Literature 1:
    Japanese Patent No. 3741455
Patent Literature 2:
    Japanese Patent No. 3264447
Patent Literature 3:
    Japanese Patent Laid-Open No. 2018-145085
Patent Literature 4:
    Japanese Patent No. 6029654
Patent Literature 5:
    U.S. Pat. No. 4,520,221
Patent Literature 6:
    U.S. Pat. No. 4,568,768

SUMMARY OF INVENTION

Technical Problem

Although a certain effect was observed in the production of aromatic hydrocarbons in the method proposed in Patent Literature 3, acid sites on the surface of zeolite were however removed. Therefore, the method still had room for improvement with respect to the production efficiency and selectivity of aromatic hydrocarbons. The method proposed in Patent Literature 4 has a problem that when the zeolite is covered with the silicate, hydrothermal synthesis is required a plurality of times. Additionally, the method is for producing p-xylene selectively, and is not considered at all with respect to the production efficiency and selectivity of aromatic hydrocarbons. The methods proposed in Patent Literatures 5 and 6 propose that the surface acid sites are covered with an amine, and the zeolites have a problem with the stability as a catalyst for producing aromatic hydrocarbons on the assumption of use at high temperature since the amine is easily desorbed or decomposed at high temperature.

Solution to Problem

Accordingly, the present inventors have earnestly investigated to solve the above-mentioned problems, consequently found that by selectively removing only the Bronsted acid sites on the surface of the zeolite, a novel 10-membered ring pore zeolite with a specific amount and small amount of Bronsted acid sites on the outer surface and a specific average particle diameter could be obtained, and that the zeolite exhibited excellent performance in the production of aromatic hydrocarbons. As the result, the present invention was completed.

That is, the present invention relates to a zeolite satisfying the following characteristics (i) to (iii) and a catalyst for producing aromatic hydrocarbons, comprising: the same.
(i) An average particle diameter is 100 nm or less.
(ii) The zeolite is a 10-membered ring pore zeolite.
(iii) A Bronsted acid amount on an outer surface is 0.1 to 10.0 µmol/g.

Hereinafter, the present invention will be described in detail.

The novel zeolite of the present invention satisfies all the requirements: (i) the average particle diameter (hereinafter occasionally described as PD) is PD≤100 nm, (ii) the zeolite is a 10-membered ring pore zeolite, and (iii) the amount of Bronsted acid sites on the outer surface is 0.1 to 10.0 µmol/g.

The novel zeolite of the present invention has (i) PD≤100 nm. It is preferable that the zeolite has 5 nm≤PD≤100 nm, since it has particularly excellent thermal stability. Here, if the PD is more than 100 nm, the conversion reaction efficiency is inferior when used as a catalyst for the conversion reaction of hydrocarbons.

The method for measuring a PD in the present invention is not limited, and examples include any method such as a method for selecting any 100 or more particles in a photograph taken under a scanning electron microscope (SEM) or a transmission electron microscope (TEM) and finding the average diameter thereof or a method for calculating the PD from the outer surface area of a zeolite using the following Expression (1):

$$PD=6/S \times (1/(2.29 \times 10^6)+0.18 \times 10^{-6}) \quad (1)$$

wherein S represents the outer surface area (m²/g). The outer surface area (S (m²/g)) in the Expression (1) can be determined from the t-plot method with use of a general nitrogen adsorption method at liquid nitrogen temperature. For example, when t is defined as the thickness of the amount of adsorption, measurement points in the t range of 0.6 to 1 nm are linearly approximated, and the outer surface area of the zeolite is determined from the slope of the obtained regression line.

Especially, the method with an SEM or a TEM is preferable, since it allows for easy measurement.

The novel zeolite of the present invention is (ii) a 10-membered ring pore zeolite. The novel zeolite of the present invention may be any zeolite as long as the zeolite is a zeolite wherein the skeleton structure has a 10-membered ring structure, and the zeolite has pores. Specific examples of the zeolite having a 10-membered ring structure include zeolites of AEL, EUO, FER, HEU, MEU, MEL, MFI, NES types, and the like. The zeolite is preferably an MFI type or an MEL type, since the zeolite is expected to be particularly effective as a catalyst for producing aromatic hydrocarbons. Examples of the MFI type include aluminosilicate compounds which belong to the structure code MFI defined by the International Zeolite Association.

The novel zeolite of the present invention has (iii) a Bronsted acid amount (hereinafter occasionally described as a B acid amount) of 0.1 to 10.0 µmol/g on the outer surface. Since the zeolite has a B acid amount on the outer surface in the said specific range, the zeolite exhibits particularly excellent catalyst performance at the time of using the zeolite as a catalyst for producing aromatic hydrocarbons. Here, when the B acid amount on the outer surface is less than 0.1 µmol/g, the zeolite is inferior in the catalyst performance of production efficiency and selectivity at the time of using the zeolite as a catalyst for producing aromatic hydrocarbons. Meanwhile, when the B acid amount on the outer surface is more than 10.0 µmol/g, side reactions on the surface of the catalyst and coking occur easily, and the catalyst performance deteriorates.

It is preferable that the novel zeolite of the present invention have (iv) the B acid amount of 0.1 to 1.0 mmol/g, since this results in a catalyst with excellent production efficiency and selectivity of aromatic hydrocarbons when used as a catalyst for producing aromatic hydrocarbon.

Here, the B acid amount of a zeolite represents the amount of Bronsted acid sites (hereinafter occasionally described as B acid sites), and represents acidic OH groups existing in the zeolite. A zeolite usually has B acid sites on the outer surface and in (micro)pores. The zeolite having only few B acid sites means that a zeolite has almost all the B acid sites in (micro)pores.

As a method for confirming the B acid amount on the outer surface in the novel zeolite of the present invention, as long as it can be confirmed, any method can be used. For example, the B acid amount can be confirmed by the adsorption of 2,4-dimethylquinoline, which has adsorptivity to B acid sites. Then, 2,4-dimethylquinoline has the property of adsorbing to B acid sites (acidic OH groups) which exists in a zeolite (including the insides of pores). However, when the (micro)pore diameter of a zeolite is smaller than a 2,4-dimethylquinoline molecule like the MFI type, the molecule cannot enter a (micro)pore, or cannot adsorb to a B acid site in a (micro)pore. That is, 2,4-dimethylquinoline adsorbs to only B acid sites on the outer surface of a zeolite. Therefore, the B acid amount on the outer surface can be quantified by determining the amount of 2,4-dimethylquinoline adsorbed to the B acid sites on the outer surface of the MFI type zeolite.

As a more specific method, the infrared absorption spectrum of a zeolite subjected to deaeration and dehydration treatments at 400° C. for 2 hours as the pretreatment of the zeolite is measured at 150° C. Then, 2,4-dimethylquinoline gas is introduced to the zeolite subjected to deaeration and dehydration treatments and adsorbed for 30 minutes. Then, surplus 2,4-dimethylquinoline is removed by exhaustion at 150° C. to prepare a zeolite to which 2,4-dimethylquinoline is adsorbed, and the infrared absorption spectrum at 150° C. is measured. That is, in the difference spectrum of the infrared absorption before and after the adsorption of 2,4-dimethylquinoline, the B acid amount on the outer surface can be obtained by quantifying the difference (decrease) in infrared absorption in the range of 3600 to 3650 cm$^{-1}$. Although 2,4-dimethylquinoline also adsorbs to silanol sites on the surface of the zeolite, the absorption derived from the O—H stretching vibration of silanol is observed at 3700 to 3800 cm$^{-1}$. Meanwhile, the absorption derived from the O—H stretching vibration of B acid sites on the outer surface of a zeolite is observed at 3600 to 3650 cm$^{-1}$, and the adsorption of 2,4-dimethylquinoline on the B-acid sites decreases the infrared absorption spectrum in the range of 3600 to 3650 cm$^{-1}$ where the absorption derived from the O—H stretching vibration of the B-acid sites is observed. That is, the decrease in the infrared absorption spectrum in the range of 3600 to 3650 cm$^{-1}$ indicates the adsorption of 2,4-dimethylquinoline to the B-acid sites on the outer surface of the zeolite.

As a method for measuring the B acid amount of the novel zeolite of the present invention (B acid sites existing on the outer surface and in (micro)pores), as long as it can be measured, any method can be used. For example, the B acid amount can be confirmed by the adsorption of pyridine, which has adsorptivity to B acid sites. Pyridine has the property of adsorbing to B acid sites (acidic OH groups) existing on the zeolite (including the inside of pores). When the (micro)pore diameter of the zeolite is larger than pyridine, pyridine can enter (micro)pores, and can also adsorb to the B acid sites on the outer surface and in (micro)pores. Therefore, the B acid amount existing in the zeolite also including the B acid amount of the B acid sites existing in the pores of the MFI type zeolite can be quantified.

As a more specific method, the infrared absorption spectrum of the zeolite subjected to deaeration and dehydration treatments at 400° C. for 2 hours as the pretreatment of the zeolite is measured at 150° C. Then, pyridine gas is introduced to the zeolite subjected to deaeration and dehydration treatments and adsorbed for 10 minutes. Surplus pyridine is removed by exhaustion at 150° C. to prepare a zeolite to which pyridine is adsorbed, and the infrared absorption spectrum at 150° C. is measured. That is, in the difference spectrum of the infrared absorption before and after the adsorption of pyridine, the B acid amount also including the insides of pores can be obtained by quantifying the difference (decrease) in infrared absorption in the range of 1515 to 1565 cm$^{-1}$.

Especially, it is preferable that the novel zeolite in the present invention is a zeolite having few B acid sites on the outer surface and almost all the B acid sites in (micro)pores, since the zeolite is a catalyst with excellent production efficiency and selectivity of aromatic hydrocarbons when used as the catalyst for producing aromatic hydrocarbon. The B acid sites on the outer surface thereof are preferably 1 to 10% of all the B acid sites. The proportion of the B acid sites on the outer surface is determined as the ratio of the B acid amount on the outer surface of the above-mentioned zeolite to the B acid amount existing on the zeolite (including the insides of pores).

As a method for producing the novel zeolite of the present invention, as long as the zeolite which satisfies the characteristics described in the above-mentioned (i) to (iii) can be produced, any method can be used. Examples of a method for producing a zeolite having a specific amount and small amount of B acid sites on the outer surface, namely a method for removing the B acid sites on the surface of the zeolite selectively include a method in which a part or all of the calcinating treatment when the zeolite which satisfies the characteristics (i) to (ii) is produced is changed into hydrothermal (steam) treatment, and ion exchange treatment is added before and after the calcinating treatment.

General and well-known method can be used for synthesis of the zeolite that satisfies the properties of (i) to (ii), which can be made into a zeolite having PD 100 nm and a 10-membered ring pore skeleton structure. Specifically, the zeolite can be produced by calcinating a crystalline material obtained by mixing a compound containing an alkali metal and/or an alkaline-earth metal as a cation, an organic structure-directing agent, and aluminosilicate gel. Examples of the compound containing an alkali metal and/or an alkaline-earth metal in that case include sodium hydroxide, potassium hydroxide, calcium hydroxide, and magnesium hydroxide, and sodium hydroxide is particularly preferable. Examples of the organic structure-directing agent include tetrapropylammonium hydroxide, tetrabutylammonium hydroxide, and tetraethylammonium hydroxide. Examples of the aluminosilicate gel include amorphous aluminosilicate gel.

Furthermore, when a zeolite which satisfies the characteristics (i) to (iii) is prepared, a method in which ion exchange is performed before calcination of the crystalline material obtained by the above method, calcination in which part or all of the calcination is changed into hydrothermal treatment is performed, and then ion exchange is further performed can be used. It is also possible to prepare the zeolite which satisfies the characteristics (i) to (iii) by a method in which the crystalline material obtained by the above method is calcinated, followed by ion exchange to make proton-type zeolite, and then calcinated under a hydrothermal atmosphere.

As calcinating conditions in that case, the treatment temperature is preferably 300 to 900° C., and particularly preferable 400 to 700° C. Treatment time is preferably 5 minutes to 25 hours industrially. Examples of the atmosphere also include one of nitrogen, air, oxygen, argon, other inert gas, or gas in combination of two or more. Aluminum at B acid sites is desorbed by performing a part or all of the calcinating step by hydrothermal (steam) treatment. The treatment temperature of the hydrothermal treatment is preferably 400 to 750° C., and particularly preferably 500 to 650° C. The concentration of steam is preferably 5 to 100%, and particularly preferably 10 to 80%.

Ion exchange is performed before and after the calcinating step, and may be divided into a plurality of ion exchange steps and performed. Examples of ionic exchange include ionic exchange using ammonium chloride or an acid such as hydrochloric acid or nitric acid, and ion exchange using hydrochloric acid or nitric acid is preferable. Washing with water can also be substituted for the ion exchange.

Since the novel zeolite of the present invention has an action as a catalyst which is excellent in the productivity and selectivity at the time of aromatic hydrocarbon manufacturing from aliphatic hydrocarbon, the novel zeolite exhibits excellent performance as a catalyst for producing aromatic hydrocarbons containing the zeolite.

When the zeolite is used as a catalyst for producing aromatic hydrocarbons, the zeolite is preferably shaped as a molded article since the zeolite is a catalyst excellent in the handleability and catalyst performance thereof. The zeolite may be molded by any method at the time of shaping, and examples include a method for molding zeolite powder into a predetermined shape by compression molding or the like as it is to form a molded article, a method for mixing a binder at a predetermined ratio into the zeolite, mixing a further additive at a predetermined ratio depending on circumstances and molding a mixture thereof into a predetermined shape to form a molded article, and a method for adding sintering to form a molded article. When the novel zeolite of the present invention is used as a catalyst for producing aromatic hydrocarbons, it is preferable that the molded article is a molded article comprising the zeolite and a binder. This molded article has excellent moldability as a molded article, exhibits high crushing strength, and also has excellent handleability and catalyst life. Further, when the novel zeolite of the present invention is used as a catalyst for producing aromatic hydrocarbons, it is more preferable that the molded article is a molded article comprising the zeolite and silica. This molded article exhibits better catalyst performance. As long as the silica in that case belongs to a category called silica, the silica may be any silica, and the silica may have a specific crystal structure, or may be amorphous. Furthermore, the particle diameter and aggregation diameter, and the like of the silica are not limited at all. The content ratio of the zeolite to silica is arbitrary. Since the molded article is a catalyst for producing aromatic hydrocarbons which exhibits particularly excellent catalyst performance, handleability, and catalyst life among others, it is preferable that the zeolite:silica=50 to 95:50 to 5 (weight ratio), and it is more preferable that the ratio be 60 to 90:40 to 10.

The catalyst for producing aromatic hydrocarbons may be in any shape. Examples include a columnar shape, a cylindrical shape, polygonal prism shapes such as a triangular prism shape, a quadratic prism shape, a pentagonal prism shape, and a hexagonal prism shape, hollow polygonal prism shapes, and spherical shapes. Especially since the catalyst is excellent in continuous productivity, and is a catalyst having high crushing strength, the columnar shape and the cylindrical shape are preferable. Sizes such as diameter, width, and length; and densities such as bulk density, and true density can be optionally selected in view of packing efficiency and the like. Especially since the catalyst is a catalyst which enables producing aromatic hydrocarbons effectively, the catalyst preferably has a columnar shape with a diameter of 1 to 10 mm or a cylindrical shape with a thickness of 0.5 to 5.0 mm. Moreover, any metal species may be introduced into the catalyst for producing aromatic hydrocarbons by treatment such as supporting, ion exchange, physical mixing, or vapor deposition.

The catalyst for producing aromatic hydrocarbons enables producing aromatic hydrocarbons particularly efficiently, for example, in contact with non-aromatic hydrocarbons having 4 to 6 carbon atoms as raw materials. To produce aromatic hydrocarbons more highly efficiently, the non-aromatic hydrocarbon raw materials comprise preferably 20 percent by mass or more, more preferably 50 percent by mass or more, and further preferably 70 percent by mass non-aromatic hydrocarbons with 4 to 6 carbon atoms. As long as the non-aromatic hydrocarbons with 4 to 6 carbon atoms in that case belong to the category thereof, the non-aromatic hydrocarbons with 4 to 6 carbon atoms may be any non-aromatic hydrocarbon. Examples include saturated aliphatic hydrocarbons, unsaturated aliphatic hydrocarbons, alicyclic hydrocarbons, and a mixture thereof. More specific examples include n-butane, isobutane, 1-butene, 2-butene, isobutene, butadiene, cyclobutene, cyclobutane, n-pentane, 1-pentane, 2-pentane, 1-pentene, 2-pentene, 3-pentene, n-hexane, 1-hexane, 2-hexane, 1-hexene, 2-hexene, 3-hexene, hexadiene, cyclohexane, and a mixture thereof. Raw material components other than non-aromatic hydrocarbons with 4 to 6 carbon atoms contained in raw materials depending on circumstances may be any compounds as long as the raw material components are compounds containing a carbon component. Examples include hydrocarbons with 1 to 3 carbon atoms, hydrocarbons with 7 to 15 carbon atoms, oxygen-containing compounds (alcohols, ethers, carboxylic acids, ketones, and the like), and nitrogen-containing compounds (amines and the like). Hydrocarbons with 1 to 3 carbon atoms or hydrocarbons with 7 to 10 carbon atoms are preferable from the viewpoint of producing aromatic hydrocarbons efficiently.

The reaction temperature thereof is not particularly limited in the production of aromatic hydrocarbons using the catalyst for producing aromatic hydrocarbons, as long as aromatic hydrocarbons may be produced. Especially since the method is a method for producing aromatic hydrocarbons efficiently which suppresses the generation of olefins or alkanes and does not require an excessively heat-resistant reactor, the reaction temperature is desirably in the range of 400 to 800° C. The reaction pressure is not limited, either, for example, the operation is possible in the pressure range of around 0.05 MPa to 5 MPa. The amount of reaction raw materials fed to the catalyst for producing aromatic hydrocarbons is not limited as a volume ratio of raw material gas to the catalyst volume, and examples include a space velocity of around 1 $h^{-1}$ to 50000 $h^{-1}$. When hydrocarbons are fed as material gas, single gas of specific hydrocarbon, mixed gas, and these diluted with single or mixed gas selected from inert gas such as nitrogen; hydrogen; carbon monoxide; and carbon dioxide can also be used.

The reaction mode when aromatic hydrocarbons are produced is not limited, and for example, not only fixed beds, transport beds, fluidized beds, movable beds, and multitubular reactors but also continuous flow, intermittent flow, and swing reactors, and the like can be used.

As long as the aromatic hydrocarbon to be produced belongs to a category called aromatic hydrocarbons, the aromatic hydrocarbon is not particularly limited. Examples include benzene, toluene, xylene, trimethylbenzene, ethylbenzene, propylbenzene, butylbenzene, naphthalene, and methylnaphthalene, and especially the aromatic hydrocarbon is preferably benzene, toluene, or xylene.

Advantageous Effects of Invention

When a novel 10-membered ring pore zeolite of the present invention having a specific average particle diameter and a very small amount of the B acid amount on the outer surface is used as a catalyst for producing aromatic hydrocarbons, aromatic hydrocarbons can be produced with excellent production efficiency and selectivity. The industrial usefulness thereof is expected.

EXAMPLES

Figure 1:
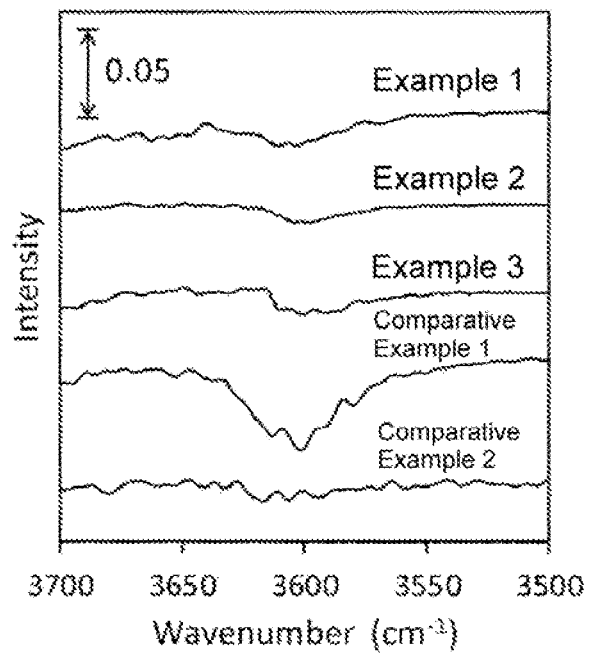
FIG. 1 is a figure showing infrared absorption spectra of zeolites obtained in Examples 1, 2, and 3 and Comparative Examples 1 and 2 (before and after 2,4-dimethylquinoline adsorption).

Although the present invention will be described with the Examples specifically hereinafter, the present invention is not limited to these Examples.

In addition, 10-membered ring pore zeolites used for the Examples and the Comparative Examples were prepared based on Japanese Patent No. 6070336. Zeolites and catalysts for producing aromatic hydrocarbons were measured by the following methods.

—Measurement of Average Particle Diameter—

The average particle diameter was measured under a transmission electron microscope (hereinafter occasionally described as a TEM) and a scanning electron microscope (hereinafter occasionally described as a SEM). A transmission electron microscope (manufactured by JEOL Ltd., (trade name) JEM-2100, accelerating voltage: 200 kV, observation magnification: 30,000) was used as the TEM. A substance obtained by ultrasonically dispersing a sample lightly ground in a mortar in acetone, dropping the mixture on a plastic supporting film, and air drying the dropped mixture was prepared as a sample for microscopic examination, and a photograph was taken. As to each of the first particles in a photograph, the average of the longest diameter and a diameter perpendicular at the middle point thereof was measured, and the average of a total of 300 particles was defined as an average particle diameter. A scanning electron microscope (manufactured by KEYENCE CORPORATION, (trade name) VE-9800, accelerating voltage: 20 kV, observation magnification: 2,000) was used as the SEM. A substance obtained by placing a sample lightly ground in the mortar on a sample stand and vapor-depositing gold on the ground sample was prepared as a sample for microscopic examination, and a photograph was taken.

Then, the length of one side of each of 150 particles in the photograph was measured, and the average value thereof was defined as an average crystal diameter.

—Infrared Absorption Spectrometry by 2,4-dimethylquinoline Adsorption—

The infrared absorption spectrum was measured using an FT-IR measuring device ((trade name) FT/IR-6700, manufactured by JASCO Corporation) by the transmission method. The spectrum was obtained at an integrated number of 256 using an MCT detector. A sample was molded into a disk having a diameter of 13 mm, then installed in a disk holder in a vacuum deaeration cell made of quartz and installed in the infrared light path perpendicularly thereto. As the pretreatment of the sample, the temperature was raised to 400° C. at 10° C./minute under vacuum exhaustion, and maintained for 2 hours. After cooling to 150° C., the infrared absorption spectrum before 2,4-dimethylquinoline adsorption was measured. Then, 2,4-dimethylquinoline gas was introduced and adsorbed for 30 minutes, vacuum exhaustion was performed at 150° C. for 1 hour, and the infrared absorption spectrum after 2,4-dimethylquinoline adsorption was then measured. The difference between the infrared absorption spectrum after the 2,4-dimethylquinoline adsorption and the spectrum before the adsorption was made, and a change in infrared absorption due to adsorption was measured. In this difference spectrum, a peak near 3600 $cm^{-2}$ was an absorption spectrum peak of 2,4-dimethylquinoline adsorbing to Bronsted acids, this area intensity was found, the B acid amount was then found from the following Expression (2) according to Lambert-Beer's law. B acid amount ($\mu$mol/mg)=A·S/(W·$\epsilon$) Expression (2) wherein the above-mentioned letters represent as follows: A: peak area strength of objective peak ($cm^{-2}$), S: sample cross section area ($cm^2$), W: sample weight (mg), and $\epsilon$: integrated absorption coefficient is 3.7 cm·$\mu$mol$^{-2}$.

—Infrared Absorption Spectrometry of Pyridine Adsorption—

In the above-mentioned infrared absorption spectrometry of 2,4-dimethylquinoline adsorption, the measurement is performed using the same device and the same technique except only that pyridine gas was introduced and adsorbed for 10 minutes.

However, the peak near 1545 $cm^{-1}$ in the difference spectrum was used as the peak of the absorption spectrum of pyridine adsorbing to Bronsted acids, the integrated absorption coefficient was 1.67 cm·$\mu$mol$^{-1}$, and the B acid amount was found from the above-mentioned Expression (2).

—Measurement of Shortest Distance from Outermost Side of Molded Article to Center of Molded Article (Center of Molded Article Section) or Side of Molded Article Inner Cylinder—

First, 30 molded article particles selected at random were measured using a slide caliper, and the average thereof was defined as a measured value.

—Measurement of Powder X-Ray Diffraction—

Measurement was performed at a tube voltage of 45 kV and a tube current of 40 mA in the air atmosphere by an X-ray diffraction measuring device (manufactured by Spectris Co., Ltd., (trade name) X'pert PRO MPD) using CuK$\alpha$1. The range of 0.04 to 5 degrees was analyzed at 0.08 degrees/step and 200 seconds/step. The background corrected with the absorption rate of the direct beam is removed.

The crystal structure was identified by confirming whether peaks exist or not visually. A peak search program may be used as another method. A common program can be used as the peak search program. For example, the measurement result with the horizontal axis representing 2$\theta$ (degree) and the vertical axis representing intensity (a. u.) is smoothed by the expression of Savitzky and Golay and a sliding polynomial filter, and the smoothed graph is then subjected to secondary differentiation. When continuous negative values of three or more points exist at that time, it can be determined that a peak exists.

—Device for Producing Aromatic Hydrocarbons and Method for Producing the Same—

Aromatic hydrocarbons were produced by the following method using the catalysts obtained by the Examples and the Comparative Examples, and the catalysts were subjected to performance evaluation as catalysts for producing aromatic hydrocarbons.

A fixed bed gaseous phase circulation type reactor having a reaction tube made of stainless steel (inner diameter: 16 mm, length: 600 mm) was used. The middle of the reaction tube made of stainless steel was filled with a molded article, pretreatment by heating was conducted with dry air circulated, and raw material gas was then fed. A tubular furnace made of ceramic was used for heating, and the temperature of the catalyst (molded article) layer was controlled. Reaction outlet gas and reaction liquid were collected, and the gas components and the liquid components were individually analyzed using gas chromatographs. The gas components were analyzed using a gas chromatograph ((trade name) GC-1700 manufactured by Shimadzu Corporation) comprising a TCD detector and having a filler ((trade name) PorapakQ produced by Waters Corporation or (trade name) MS-5A produced by GL Sciences Inc.). The liquid components were analyzed using a gas chromatograph ((trade name) GC-2015 manufactured by Shimadzu Corporation) comprising an FID detector and having a capillary column ((trade name) TC-1 produced by GL Sciences Inc.) as a separation column.

Reaction conditions were set as follows.

(Aromatic Hydrocarbon Production Conditions)

Catalyst weight: 3.8 g

Circulation gas: Mixed gas of 50% by mol raw material gas+50% by mol nitrogen

Reaction temperature: 590° C.
(Pretreatment Conditions)
Catalyst temperature: 590° C.
Circulation gas: air at 100 Nml/minute
Treatment time: 1 hour.

Example 1

Amorphous aluminosilicate gel was added to an aqueous solution of tetrapropylammonium (hereinafter occasionally abbreviated as TPA) hydroxide and sodium hydroxide and suspended. An MFI type zeolite was added to the obtained suspension as seed crystal to prepare a raw material composition. The amount of seed crystals added in that case was 0.7% by weight based on the weight of $Al_2O_3$ and $SiO_2$ in the raw material composition. Ethanol produced as a by-product was evaporated and removed.

The composition of the raw material composition is as follows.
$SiO_2/Al_2O_3$ molar ratio=48, TPA/Si molar ratio=0.05, Na/Si molar ratio=0.16, OH/Si molar ratio=0.21, $H_2O$/Si molar ratio=10

The obtained raw material composition was sealed in an autoclave made of stainless steel and crystallized for 4 days with stirring at 115° C. to obtain a slurry-like mixed liquid. The slurry-like mixed liquid after crystallization was subjected to solid-liquid separation with a centrifuge, and the solid particles were then washed with an enough amount of pure water and dried at 110° C. to obtain a dry powder.

The obtained dry powder was dispersed in 1 mol/L hydrochloric acid at normal temperature and filtered, and the solid particles were then washed with an enough amount of pure water, filtered again and then dried at 100° C. overnight. The solid particles were calcinated in air at 550° C. for 1 hour and then treated with 30% steam at 600° C. for 2 hours.

The obtained powder was dispersed in 1 mol/L hydrochloric acid at normal temperature and filtered, and the solid particles were then washed with an enough amount of pure water and filtered again to then obtain a zeolite.

Table 1 shows the physical properties of the obtained zeolite. The obtained zeolite was a 10-membered ring pore zeolite having the skeleton structure of an MFI type zeolite, and the average particle diameter measured using a TEM was 25 nm.

Figure 2:
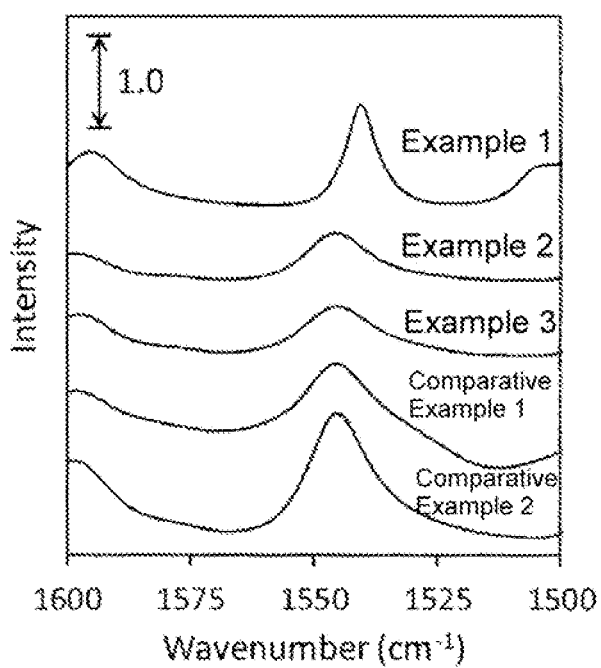
FIG. 2 is a figure showing infrared absorption spectra of zeolites obtained in Examples 1, 2, and 3 and Comparative Examples 1 and 2 (before and after pyridine adsorption).

FIG. 1 shows the difference spectrum between the infrared absorptions before and after 2,4-dimethylquinoline was adsorbed to the obtained zeolite (sample amount: 56 mg). FIG. 2 shows the difference spectrum between the infrared absorptions before and after pyridine was adsorbed (sample amount: 54 mg). The B acid amount on the outer surface found from a decrease in the peak derived from OH of the zeolite B acid sites at 3600 $cm^{-1}$ in FIG. 1 was 2.8 µmol/g. The B acid amount found from an increase in the peak derived from pyridine adsorbed to the zeolite B acid sites at 1545 $cm^{-1}$ in FIG. 2 was 0.15 mmol/g. The outer surface B acid proportion was 1.9%.

Then, 25 parts by weight of silica (produced by Nissan Chemical Corporation, (trade name) SNOWTEX N-30G), 5 parts by weight of cellulose, and 40 parts by weight of pure water were added to 100 parts by weight of the obtained zeolite, and the mixture was kneaded. The kneaded material was formed into a columnar molded article having a diameter of 1.5 mm and lengths of 1.0 to 7.0 mm (average length: 3.5 mm). This was dried at 100° C. overnight. The molded article after drying was calcinated in circulated air at 600° C. for 2 hours to obtain a molded article.

Aromatic hydrocarbons were produced under the above-mentioned conditions using the obtained molded article as a catalyst for producing aromatic hydrocarbons, and the aromatization was evaluated. The amounts of raw material gases circulated were as follows: isobutane: 2 Nml/minute, normal butane: 5 Nml/minute, trans-2-butene: 8 Nml/minute, 1-butene: 15 Nml/minute, isobutene: 3 Nml/minute, propane: 7 Nml/minute, and propylene: 2 Nml/minute. Table 2 shows the C4 component conversion, the yield of aromatic hydrocarbons, and the yield of benzene versus reaction time. All of the C4 component conversion, the aromatic yield, and the yield of benzene exhibited high values for a period of reaction time from 30 minutes to 1500 minutes.

TABLE 1

|  | Average particle diameter (nm) | B acid amount on the outer surface (µmol/g) | B acid amount (mmol/g) | Outer surface B acid proportion (%) |
|---|---|---|---|---|
| Example 1 | 25 | 2.8 | 0.15 | 1.9 |
| Example 2 | 19 | 3.0 | 0.12 | 2.5 |
| Example 3 | 24 | 5.3 | 0.13 | 4.0 |
| Comparative Example 1 | 26 | 17.3 | 0.15 | 11.2 |
| Comparative Example 2 | 2110 | 17.5 | 0.27 | 6.4 |

TABLE 2

|  | $C_4$ component conversion (%) Reaction time: 30 to 1500 minutes | Yield of aromatic compounds (wt %) Reaction time: 30 to 1500 minutes | Yield of benzene (wt %) Reaction time: 30 to 1500 minutes |
|---|---|---|---|
| Example 1 | >99 | 51 | 23 |
| Example 2 | 96 | 42 | 21 |
| Example 3 | 97 | 43 | 21 |
| Example 4 | 95 | 42 | 19 |
| Example 5 | 90 | 37 | 18 |
| Comparative Example 1 | 74 | 29 | 12 |
| Comparative Example 2 | 54 | 27 | 12 |

Example 2

The operations for crystallizing the zeolite with the autoclave, washing, and drying were performed in the same way as in Example 1. The obtained dry powder was dispersed in 1 mol/L hydrochloric acid at normal temperature and filtered. The solid particles were then washed with an enough amount of pure water, filtered again and then dried at 100° C. overnight. The solid particles were calcinated in air at 550° C. for 1 hour and then treated with 45% of steam in air at 600° C. for 3 hours.

The obtained powder was dispersed in 1 mol/L hydrochloric acid at 40° C. and filtered, and the solid particles were then washed with an enough amount of pure water, filtered again and then dried at 100° C. overnight to obtain a zeolite.

Table 1 shows the measurement results of the obtained zeolite. The obtained zeolite was a 10-membered ring pore zeolite having the skeleton structure of an MFI type zeolite, and the average particle diameter measured using a TEM was 19 nm.

FIG. 1 shows the difference spectrum between the infrared absorptions before and after 2,4-dimethylquinoline was adsorbed to the obtained MFI type zeolite (sample amount: 59 mg). FIG. 2 shows the difference spectrum between the infrared absorptions before and after pyridine was adsorbed (sample amount: 51 mg). The B acid amount on the outer surface found from a decrease in the peak derived from OH of the zeolite B acid sites at 3600 cm$^{-1}$ in FIG. 1 was 3.0 µmol/g. The B acid amount found from an increase in the peak derived from pyridine adsorbed to the zeolite B acid sites at 1545 cm$^{-1}$ in FIG. 2 was 0.12 mmol/g. The outer surface B acid proportion was 2.5%.

Then, 25 parts by weight of silica (produced by Nissan Chemical Corporation, (trade name) SNOWTEX N-30G), 5 parts by weight of cellulose, and 40 parts by weight of pure water were added to 100 parts by weight of the obtained zeolite, and the mixture was kneaded. The kneaded material was formed into a columnar molded article having a diameter of 1.5 mm and lengths of 1.0 to 7.0 mm (average length: 3.4 mm). This was dried at 100° C. overnight. The molded article after drying was calcinated in circulated air at 600° C. for 2 hours to obtain a molded article.

Aromatic hydrocarbons were produced under the above-mentioned conditions using the obtained molded article as a catalyst for producing aromatic hydrocarbons, and the aromatic hydrocarbons were evaluated. The amounts of raw material gases circulated were as follows: isobutane: 2 Nml/minute, normal butane: 5 Nml/minute, trans-2-butene: 8 Nml/minute, 1-butene: 15 Nml/minute, isobutene: 3 Nml/minute, propane: 7 Nml/minute, and propylene: 2 Nml/minute. Table 2 shows the C4 component conversion, the yield of aromatic hydrocarbons, and the yield of benzene versus reaction time. All of the C4 component conversion, the aromatic yield, and the yield of benzene exhibited high values for a period of reaction time from 30 minutes to 1500 minutes.

Example 3

The operations for crystallizing the zeolite with the autoclave, washing, and drying were performed in the same way as in Example 1.

The obtained dry powder was calcinated in air at 550° C., and the obtained powder was then dispersed in 1 mol/L hydrochloric acid at normal temperature and filtered. The solid particles were then washed with an enough amount of pure water, filtered again and dried at 100° C. overnight.

The obtained powder was calcinated in air at 550° C. for 1 hour and then treated with 20% of steam in air at 600° C. for 60 minutes.

Table 1 shows the evaluation results of the obtained zeolite. The obtained zeolite was a 10-membered ring pore zeolite having the skeleton structure of an MFI type zeolite, and the average particle diameter measured using a TEM was 24 nm.

FIG. 1 shows the difference spectrum between the infrared absorptions before and after 2,4-dimethylquinoline was adsorbed to the obtained MFI type zeolite (sample amount: 56 mg). FIG. 2 shows the difference spectrum between the infrared absorptions before and after pyridine was adsorbed (sample amount: 55 mg). The B acid amount on the outer surface found from a decrease in the peak derived from OH of the zeolite B acid sites at 3600 cm$^{-1}$ in FIG. 1 was 5.3 µmol/g. The B acid amount found from an increase in the peak derived from pyridine adsorbed to the zeolite B acid sites at 1545 cm$^{-1}$ in FIG. 2 was 0.13 mmol/g. The outer surface B acid proportion was 4.0%.

Then, 25 parts by weight of silica (produced by Nissan Chemical Corporation, (trade name) SNOWTEX N-30G), 5 parts by weight of cellulose, and 40 parts by weight of pure water were added to 100 parts by weight of the obtained zeolite, and the mixture was kneaded. The kneaded material was formed into a columnar molded article having a diameter of 1.5 mm and lengths of 1.0 to 7.0 mm (average length: 3.5 mm). This was dried at 100° C. overnight. The molded article after drying was calcinated in circulated air at 600° C. for 2 hours to obtain a molded article.

Aromatic hydrocarbons were produced under the above-mentioned conditions using the obtained molded article as a catalyst for producing aromatic hydrocarbons, and the aromatization was evaluated. The amounts of raw material gases circulated were as follows: isobutane: 2 Nml/minute, normal butane: 5 Nml/minute, trans-2-butene: 8 Nml/minute, 1-butene: 15 Nml/minute, isobutene: 3 Nml/minute, propane: 7 Nml/minute, and propylene: 2 Nml/minute. Table 2 shows the C4 component conversion, the yield of aromatic hydrocarbons, and the yield of benzene versus reaction time. All of the C4 component conversion, the aromatic yield, and the yield of benzene exhibited high values for a period of reaction time from 30 minutes to 1500 minutes.

Example 4

First, 25 parts by weight of silica (produced by Nissan Chemical Corporation, (trade name) SNOWTEX N-30G), 5 parts by weight of cellulose, and 45 parts by weight of pure water were added to 100 parts by weight of the zeolite obtained in Example 2, and the mixture was kneaded. The kneaded material was formed into a columnar molded article having a diameter of 3.0 mm and lengths of 2.0 to 9.0 mm (average length: 6.6 mm). This was dried at 100° C. overnight. The molded article after drying was calcinated in circulated air at 600° C. for 2 hours to obtain a molded article.

Aromatic hydrocarbons were produced under the above-mentioned conditions using the obtained molded article as a catalyst for producing aromatic hydrocarbons, and the aromatic hydrocarbons were evaluated. The amounts of raw material gases circulated were as follows: isobutane: 2 Nml/minute, normal butane: 5 Nml/minute, trans-2-butene: 8 Nml/minute, 1-butene: 15 Nml/minute, isobutene: 3 Nml/minute, propane: 7 Nml/minute, and propylene: 2 Nml/minute. Table 2 shows the C4 component conversion, the yield of aromatic hydrocarbons, and the yield of benzene versus reaction time. All of the C4 component conversion, the aromatic yield, and the yield of benzene exhibited high values for a period of reaction time from 30 minutes to 1500 minutes.

Example 5

First, 25 parts by weight of silica (produced by Nissan Chemical Corporation, (trade name) SNOWTEX N-30G), 5 parts by weight of cellulose, and 45 parts by weight of pure water were added to 100 parts by weight of the zeolite obtained in Example 2, and the mixture was kneaded. The kneaded material was formed into a columnar molded article having a diameter of 4.0 mm and lengths of 3.0 to 15.0 mm (average length: 11.1 mm). This was dried at 100° C. overnight. The molded article after drying was calcinated in circulated air at 600° C. for 2 hours to obtain a molded article.

Aromatic hydrocarbons were produced under the above-mentioned conditions using the obtained molded article as a catalyst for producing aromatic hydrocarbons, and the aromatic hydrocarbons were evaluated. The amounts of raw material gases circulated were as follows: isobutane: 2 Nml/minute, normal butane: 5 Nml/minute, trans-2-butene: 8 Nml/minute, 1-butene: 15 Nml/minute, isobutene: 3 Nml/minute, propane: 7 Nml/minute, and propylene: 2 Nml/minute. Table 2 shows the C4 component conversion, the yield of aromatic hydrocarbons, and the yield of benzene versus reaction time. All of the C4 component conversion, the aromatic yield, and the yield of benzene exhibited high values for a period of reaction time from 30 minutes to 1500 minutes.

Comparative Example 1

The operations for crystallizing the zeolite with the autoclave, washing, and drying were performed in the same way as in Example 1.

The obtained dry powder was calcined in air at 550° C., and the obtained powder was then dispersed in 1 mol/L hydrochloric acid at normal temperature and filtered. The solid particles were then washed with an enough amount of pure water, filtered again and dried at 100° C. overnight to obtain a zeolite.

Table 1 shows the evaluation results of the obtained zeolite. The obtained zeolite has the skeleton structure of an MFI type zeolite, and the average particle diameter measured using a TEM was 26 nm.

FIG. 1 shows the difference spectrum between the infrared absorptions before and after 2,4-dimethylquinoline was adsorbed to the obtained MFI type zeolite (sample amount: 56 mg). FIG. 2 shows the difference spectrum between the infrared absorptions before and after pyridine was adsorbed (sample amount: 56 mg). The B acid amount on the outer surface found from a decrease in the peak derived from OH of the zeolite B acid sites at 3600 $cm^{-1}$ in FIG. 1 was 17.3 µmol/g. The B acid amount found from an increase in the peak derived from pyridine adsorbed to the zeolite B acid sites at 1545 $cm^{-1}$ in FIG. 2 was 0.15 mmol/g. The outer surface B acid proportion was 11.2%.

Then, 25 parts by weight of silica (produced by Nissan Chemical Corporation, (trade name) SNOWTEX N-30G), 5 parts by weight of cellulose, and 40 parts by weight of pure water were added to 100 parts by weight of the obtained zeolite, and the mixture was kneaded. The kneaded material was formed into a columnar molded article having a diameter of 1.5 mm and lengths of 1.0 to 7.0 mm (average length: 3.6 mm). This was dried at 100° C. overnight. The molded article after drying was calcined in circulated air at 600° C. for 2 hours to obtain a molded article.

Aromatic hydrocarbons were produced under the above-mentioned conditions using the obtained molded article as a catalyst, and the aromatization was evaluated. The amounts of raw material gases circulated were as follows: isobutane: 2 Nml/minute, normal butane: 5 Nml/minute, trans-2-butene: 8 Nml/minute, 1-butene: 15 Nml/minute, isobutene: 3 Nml/minute, propane: 7 Nml/minute, and propylene: 2 Nml/minute. Table 2 shows the C4 component conversion, the yield of aromatic hydrocarbons, and the yield of benzene versus reaction time. All of the C4 component conversion, the aromatic yield, and the yield of benzene were low and inferior in catalyst performance for a period of reaction time from 30 minutes to 1500 minutes.

Comparative Example 2

First, 40 parts by weight of silica (produced by Nissan Chemical Corporation, (trade name) SNOWTEX N-30G), 5 parts by weight of cellulose, and 40 parts by weight of pure water were added to 100 parts by weight of a proton type MFI type zeolite powder (produced by Tosoh Corporation, trade name: HSZ-840HOA; average particle diameter by SEM observation: 2110 nm, B acid amount: 0.27 mmol/g, B acid amount on the outer surface: 17.5 µmol/g, outer surface B acid proportion: 6.4%), and the mixture was kneaded. The kneaded material was formed into a columnar molded article having a diameter of 1.5 mm and lengths of 1.0 to 7.0 mm (average length: 3.5 mm). This was dried at 100° C. overnight. The molded article after drying was calcined in circulated air at 600° C. for 2 hours to obtain a molded article.

Then, 15 mg of the sample was measured for the difference spectrum between the infrared absorptions before and after 2,4-dimethylquinoline was adsorbed in FIG. 1, and 60 mg of the sample was measured for the difference spectrum between the infrared absorptions before and after pyridine was adsorbed in FIG. 2.

Aromatic hydrocarbons were produced under the above-mentioned conditions using the obtained molded article as a catalyst, and the aromatization was evaluated. The amounts of raw material gases circulated were as follows: isobutane: 2 Nml/minute, normal butane: 5 Nml/minute, trans-2-butene: 8 Nml/minute, 1-butene: 15 Nml/minute, isobutene: 3 Nml/minute, propane: 7 Nml/minute, and propylene: 2 Nml/minute. Table 2 shows the C4 component conversion, the yield of aromatic hydrocarbons, and the yield of benzene versus reaction time. All of the C4 component conversion, the aromatic yield, and the yield of benzene were low and inferior in catalyst performance for a period of reaction time from 30 minutes to 1500 minutes.

INDUSTRIAL APPLICABILITY

A novel microcrystal medium pore zeolite of the present invention having a small amount of the B acid amount on the outer surface exhibits specific stability and efficiency, for example, at the time of the conversion and isomerization reaction, especially aromatization, of hydrocarbon raw materials such as lower olefins. The industrial value thereof as a catalyst is very high.

The invention claimed is:

1. A zeolite satisfying the following characteristics (i) to (iii):
   (i) an average particle diameter is 100 nm or less,
   (ii) the zeolite is a 10-membered ring pore zeolite, and
   (iii) a Bronsted acid amount on an outer surface is 0.1 to 10.0 µmol/g.

2. The zeolite according to claim 1, wherein the 10-membered ring pore zeolite is an MFI type or an MEL type.

3. The zeolite according to claim 1, wherein the zeolite satisfies the following characteristic (iv):
   (iv) a Bronsted acid amount of 0.1 to 1.0 mmol/g.

4. A catalyst for producing aromatic hydrocarbons, comprising the zeolite according to claim 1.

5. The catalyst for producing aromatic hydrocarbons according to claim 4, further comprising silica.

6. The catalyst for producing aromatic hydrocarbons according to claim 4, wherein the catalyst is a molded article having a columnar shape or a cylindrical shape.

7. The catalyst for producing aromatic hydrocarbons according to claim 6, wherein the catalyst is a molded article having a columnar shape with a diameter of 1 to 10 mm.

8. The catalyst for producing aromatic hydrocarbons according to claim 6, wherein the catalyst is a molded article having a cylindrical shape with a thickness of 0.5 to 5.0 mm.

9. A method for producing aromatic hydrocarbons, comprising contacting a raw material comprising at least 70 percent by mass non-aromatic hydrocarbons having 4 to 6 carbon atoms with the catalyst for producing aromatic hydrocarbons according to claim 4.

\* \* \* \* \*